(12) United States Patent
Furner et al.

(10) Patent No.: US 8,047,837 B2
(45) Date of Patent: Nov. 1, 2011

(54) CANDLE WITH LID FOR DISPENSING AN AIR TREATMENT CHEMICAL

(75) Inventors: Paul E. Furner, Racine, WI (US); William G. Madala, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 494 days.

(21) Appl. No.: 11/770,259

(22) Filed: Jun. 28, 2007

(65) Prior Publication Data

US 2009/0004614 A1    Jan. 1, 2009

(51) Int. Cl.
*F23D 3/16* (2006.01)
*A62B 7/08* (2006.01)

(52) U.S. Cl. ........ 431/291; 431/292; 431/293; 431/289; 422/125

(58) Field of Classification Search .................. 431/291, 431/292, 293, 289; 362/447; 422/125
See application file for complete search history.

(56) References Cited

U.S. PATENT DOCUMENTS

| | | | |
|---|---|---|---|
| 2,237,523 A | 4/1941 | Damon | |
| 2,254,906 A | 9/1941 | Petrulis | |
| 2,742,342 A | 4/1956 | Dew et al. | |
| 2,775,006 A | 12/1956 | Kranc | |
| 3,279,118 A | 10/1966 | Allen | |
| 3,285,694 A | 11/1966 | Marchi | |
| 4,781,895 A | 11/1988 | Spector | |
| 5,911,955 A | 6/1999 | Fullam | |
| 6,033,212 A | 3/2000 | Bonnema et al. | |
| 6,144,801 A | 11/2000 | Lehoux et al. | |
| 6,152,728 A | 11/2000 | Griffel | |
| 6,231,336 B1 | 5/2001 | Chen | |
| 6,254,248 B1 * | 7/2001 | McAuley et al. | 362/101 |
| 6,309,986 B1 | 10/2001 | Flashinski et al. | |
| 6,337,080 B1 | 1/2002 | Fryan et al. | |
| 6,482,365 B1 | 11/2002 | Soller | |
| 6,503,459 B1 | 1/2003 | Leonard et al. | |
| 6,585,510 B2 * | 7/2003 | Papai | 431/291 |
| 6,589,047 B1 * | 7/2003 | Papai | 431/291 |
| 6,663,384 B2 * | 12/2003 | Papai | 431/289 |
| 6,663,838 B1 | 12/2003 | Soller et al. | |
| 7,138,130 B2 | 11/2006 | Davis et al. | |
| 7,247,017 B2 * | 7/2007 | Furner | 431/292 |
| 7,377,772 B2 * | 5/2008 | Thune et al. | 431/291 |
| 2003/0086815 A1 * | 5/2003 | Wesley | 422/5 |

OTHER PUBLICATIONS

International Search Report and Written Opinion dated Oct. 22, 2008, Appl. No. PCT/US2008/008025.

* cited by examiner

*Primary Examiner* — Kenneth Rinehart
*Assistant Examiner* — Chuka C Ndubizu

(57) ABSTRACT

Candles are provided for dispensing air treatment chemicals in response to heat. There is a lid bearing the air treatment chemical. The candle includes a housing with a combustible fuel. An upper lid includes a cover plate bearing the air treatment chemical and an opening centrally disposed in the plate to allow heated air to pass through when the fuel is being combusted. The plate is suspended across an upper end of a side wall of the housing creating an air gap adjacent the radial periphery of the lid. When the fuel is combusted the air treatment chemical can be heated thereby and carried away by heated air that has passed through the central opening, and the air gap can permit cooler air to enter the cavity while the fuel is being combusted.

8 Claims, 6 Drawing Sheets

CANDLE WITH LID FOR DISPENSING AN AIR TREATMENT CHEMICAL

CROSS-REFERENCE TO RELATED APPLICATIONS

Not applicable.

STATEMENT REGARDING FEDERALLY SPONSORED RESEARCH/DEVELOPMENT

Not applicable.

BACKGROUND OF THE INVENTION

The present invention relates to candles that dispense an air treatment chemical from a lid. More particularly, the invention relates to structures associated with the lid to facilitate such dispensing.

A variety of devices are known for dispensing volatilizable air treatment chemicals. Such air treatment chemicals may be air scents or deodorizers (e.g., fragrances or masks), pest control materials (e.g., insecticides, insect repellants, or insect growth control regulators), allergen control ingredients, disinfectants, sanitizers or other materials.

In some of these devices the air treatment chemical is mixed with a candle wax and is dispensed during the burning process, the chemical usually being released primarily from the heated wax surrounding the wick rather than from the wax as it combusts. While this is a common technique for dispensing a variety of fragrances, typically it has been less successful for the dispensing of pest control materials.

There has been a variety of attempts to improve candle burning efficiency by placing a cover over the candle. For example, see U.S. Pat. Nos. 6,585,510, 6,589,047, and 6,663,384. The disclosures of these patents and of all other publications referred to herein are incorporated herein by reference as if fully set forth herein. These devices, however, were focused on improving candle burning efficiency in a deep-cup type candle, rather than distributing air treatment chemicals from sources other than the wax.

Many other attempts have been made to use the heat from a candle or analogous device to distribute air treatment chemicals, such as U.S. Pat. Nos. 2,742,342, 4,781,895, 6,482,365, 6,503,459, and 7,138,130. However, these devices can require relatively expensive constructions to achieve their results, and/or incorporate structures that do not provide the flexibility either to distribute the air treatment chemical when the candle is on, or not to distribute the air treatment chemical even when the candle is combusting.

Other devices for using candles or similar structures to dispense volatiles are disclosed in U.S. Pat. Nos. 3,279,118, 6,033,212, 6,309,986, 6,337,080 and 6,663,838. Each has its own limitations.

Thus, there is a need for improved candle assemblies, particularly where the candle can be readily converted from normal operation to operation where the candle also dispenses an air treatment chemical.

BRIEF SUMMARY OF THE INVENTION

In one aspect the invention provides an article for dispensing an air treatment chemical. The air treatment chemical may be selected from volatile pest control agents, fragrances, deodorizers, allergen control ingredients, disinfectants, sanitizers, or other volatile materials to be dispensed.

The article includes a housing having an internal cavity into which is positioned a combustible fuel. In preferred forms, the fuel is wax burned in the form of a candle having a wick. The housing further includes a side wall structure and an upper lid. The lid has a cover plate bearing and/or supporting the air treatment chemical, the lid also having an opening centrally disposed that is suitable to allow heated air to pass through the opening when the fuel is being combusted. The cover plate is suspended across an upper end of the side wall structure with an air gap at the periphery of the plate.

The air gap may be created by providing legs, stand-offs, or similar projections on either the plate or the side wall structure to space the plate above the upper end of the side wall. Alternatively, the air gap may be created by a plurality of holes formed in the plate near its periphery or holes formed in the housing side wall. Such holes in the plate may be created by forming a portion of the plate near its periphery from a screen or open mesh.

When the fuel is combusted, the air treatment chemical is heated, volatized, and carried away by heated air passing through the central opening. The air gap permits cooler air to enter the cavity in a relatively turbulence-free manner, supporting the combustion of the fuel and creating a controlled air flow pattern, down at the periphery of the housing and up through the central opening.

The plate may itself be impregnated or coated with the air treatment chemical, or it may support a separate substrate impregnated or coated with the chemical, the substrate being in the form, for example, of a ring that surrounds the central opening or a sleeve that lines the central opening. In a preferred form, the plate includes an undulation along an upper surface of the plate, and the air treatment chemical is mounted in the undulation. Alternatively, a central annular rim around the central opening can serve to center and hold a substrate in the form of a ring in place surrounding the opening.

The fuel may have mixed therein a second air treatment chemical that is different from the air treatment chemical of the cover plate. For example, the second air treatment chemical may be a fragrance, and the air treatment chemical of the cover plate may be an insect control agent.

The housing may be any desired shape in top view, including housings that are cylindrical or essentially rectangular in top view.

In another aspect, the invention provides a kit for selectively treating air in a room with alternative chemicals. The kit includes a housing having a side wall structure and an internal cavity in which is positioned a combustible fuel. A first lid and a second alternative lid are included. Each lid comprises a cover plate bearing a selected air treatment chemical and an opening centrally disposed in the plate suitable to allow heated air to pass through the opening when the fuel is being combusted and that plate is mounted on the housing.

Each plate can be suspended across an upper end of the side wall structure with an air gap provided at the periphery of the plate, as described, above. When the fuel is combusted, the air treatment chemical of a lid being used with the housing can be heated thereby and carried away by the heated air. The air gap can permit cooler air to enter the cavity while the fuel is being combusted. The air treatment chemical of the cover plate of the first lid can be selected to be a different air treatment chemical than the air treatment chemical of the cover plate of the second lid, allowing a user to select the lid and therefore the air treatment chemical to be dispensed.

In a further aspect, the invention provides a kit including a multiplicity of substrates, each impregnated or coated with a selected air treatment chemical, each substrate being so formed as to be replaceably held surrounding a central opening of the cover plate of a lid for a housing containing a candle or other combustible fuel.

In yet another a further aspect, the invention provides a lid for use with the article for dispensing an air treatment chemical discussed above. The lid includes a cover plate bearing an insect control air treatment chemical and an opening centrally disposed in the plate suitable to allow heated air to pass through. The plate can be suspended across an upper end of the article for dispensing an air treatment chemical. The plate also has an air gap at its periphery to permit cooler air to enter the housing if the lid is used with the housing and the article fuel is being combusted.

In another preferred form, a depressed pocket is formed in the plate adjacent the opening and a supply of the air treatment chemical is mounted in the pocket.

It will be appreciated from the discussions above and below that the present invention provides a way of letting a candle function as a conventional candle (with or without an air treatment chemical, such as a fragrance, mixed in the wax). It then provides a removable lid that at various occasions can convert the candle to, for example, an insect control device. For instance, a single candle can provide light or ambiance indoors, along with a pleasant fragrance. Then, it can be moved outdoors during a picnic in the evening to both provide light and insect control by the addition of a cover plate bearing an insect control air treatment chemical. The device is inexpensive to produce and reliable.

These and still other advantages of the present invention will be apparent from the description which follows and the accompanying drawings. In them reference is made to certain preferred example embodiments. However, the claims should be looked to in order to judge the full scope of the invention, and the claims are not to be limited to just the example or preferred embodiments.

DETAILED DESCRIPTION OF THE PREFERRED EMBODIMENTS

Figure 1:
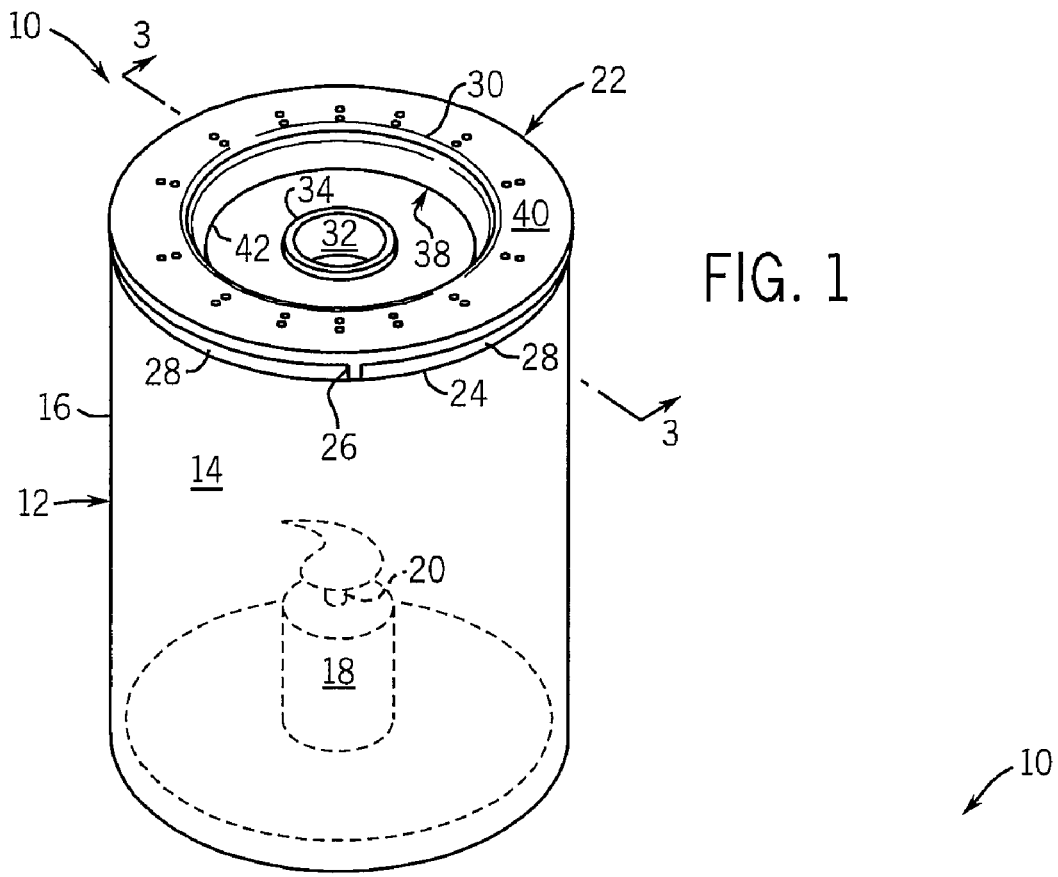
FIG. 1 is a perspective view of a first embodiment of the present invention showing a candle having a lid bearing an air treatment chemical.
Figure 2:
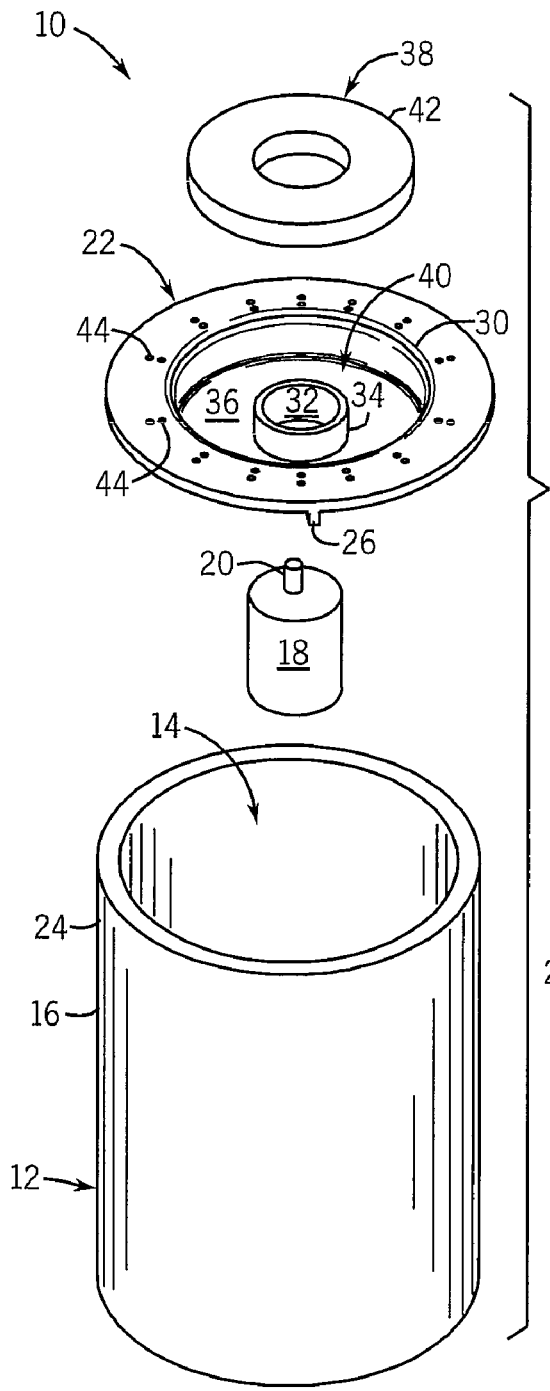
FIG. 2 is an exploded perspective view thereof.

Referring first to FIGS. 1 and 2, an article for dispensing an air treatment chemical is shown in the form of a candle 10, which is shown having a housing 12 with an internal cavity 14 and a radially peripheral outer side wall 16. The housing 12 may be made of plastic, glass, metal, or any other material suitable for use as a candle container. However, where it is desired for the candle to also provide light to an area, the side wall 16 is preferably transparent or translucent.

The candle 10 includes a fuel in the form of wax 18 and has an ignitable wick 20. Alternatively, the candle 10 may be replaced by a lamp or other fuel burner burning such fuels as butane, oil, kerosene, or the like.

Figure 3:
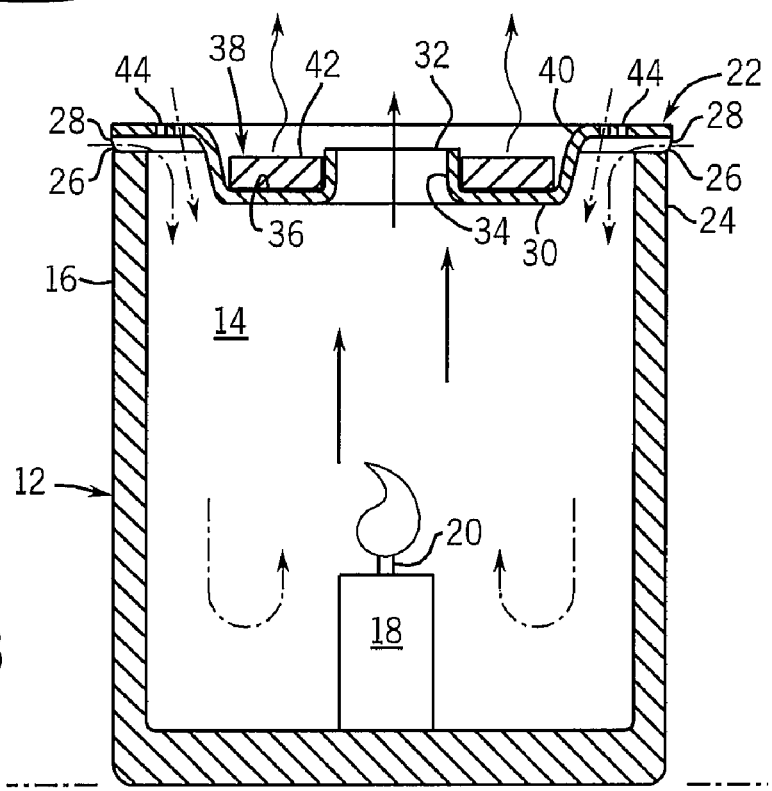
FIG. 3 is a vertical sectional view along line 3-3 of FIG. 1.

Turning now also to FIG. 3, it can be seen that the candle 10 also includes a lid 22 suspended across an upper end 24 of the side wall 16. The lid 22 has a peripheral air gap 28 formed, in this example, by a plurality of legs/standoffs 26 positioned around the periphery of the lid 22 and apertures 44 formed in the lid at its periphery. Either the standoffs 26 or the apertures 44 may be used by themselves to form the air gap 28. Alternatively, the apertures 44 may be in the form of the openings in a screen or similar reticulated structure (not shown). Also alternatively, the air gap 28 may be defined by cutouts (not shown) formed in the upper end 24 of the side wall 16, or various other combinations of these features to allow fresh air to enter the cavity 14. The air gap 28 allows external air to communicate with the internal cavity 14.

In any event, the lid 22 has a cover plate 30 having an opening 32 centrally disposed in the lid 22. The opening 32 need not be circular as shown, but may take on any suitable shape, such as rectangular, octagonal, and the like. The outer periphery of the lid is preferably made from a thermal-set epoxy or thermoset polymer.

The plate 30 has a central annular rim 34 about the perimeter of the opening 32. The plate 30 and rim 34 define an annular pocket 36 for bearing an air treatment chemical 38 held by a substrate that, in the embodiment of FIGS. 1-3, is in the form of a washer-like ring 42 adjacent an upper surface 40 of the plate 30. The ring 42 is preferably made of a porous material that can be impregnated or coated with the air treatment chemical, such as a non-woven, compressed cellulosic material, a ceramic material, or the like. Alternatively, the plate can directly hold or be coated with the air treatment chemical 38.

The portion of the plate proximate the rim 34 and the rim 34 itself are preferably made of aluminum owing to its low resistance to heat transfer. Preferably, the ring 42 is removable from the lid 22 to allow for easy transition between rings holding different types of air treatment chemicals 38 or the use of successive rings holding the same air treatment chemical.

The air treatment chemicals 38 may be selected from a wide variety of formulations. See, for example, U.S. Pat. Nos. 6,309,986 and 6,337,080 for a disclosure of many insect control materials, deodorizers, fragrances, sanitizers, and disinfectants known to be suitable for use with heating dispensers. There may be a hydrocarbon solvent having a high boiling point (as a carrier), one or more actives (e.g., an insecticide), and optionally an antioxidant and a fragrance. The formulation will be tailored for the application, and may have a variety of different ingredients as is conventional for the application.

Depending on the temperature experienced by the air treatment chemical 38, relatively high vapor pressure actives such as metofluthrin or transfluthrin can be effectively delivered at temperatures of about sixty to seventy-two degrees Celsius. Air treatment chemicals such as d-cis/trans allethrin can be effectively delivered at higher temperatures from about 125° C. to about 150° C. Also, the air treatment chemical 38 may include scents or deodorizers (e.g., fragrances or masks), pest control materials (e.g., insecticides, insect repellants, or insect growth control regulators), allergen control ingredients, disinfectants, sanitizers, mildew counteractants, and the like.

In operation, the wick 20 of the candle 10 is lit causing the air within the internal cavity 14 to heat up. The warmed air travels upward (shown by the solid, straight arrowhead lines in FIG. 3) through the chimney-like opening 32. The warmed air causes the plate 30, especially near the opening 32, to heat up and the air treatment chemical 38 to volatize at an increase rate (shown by the solid, wavy arrowhead lines in FIG. 3). At the same time, cooler ambient air enters the internal cavity 14 via the air gap 28 (shown by the dashed arrowhead lines in FIG. 3). This exchange of air creates a convection current within the candle 10 that helps disperse the volatized air treatment chemical 38 into the surrounding environment.

The amount of air treatment chemical 38 applied to the ring 42 can be selected so as to be depleted just as the wax 18 is depleted. Alternatively, the amount of wax can be made large enough to be sufficient to deliver the air treatment chemical from several successive rings 42. In that case, a use-up cue (e.g., a color changing dye) can be added to the ring 42 to visually signal the user that the air treatment chemical 38 has been depleted and the ring should be replaced.

Figure 4:
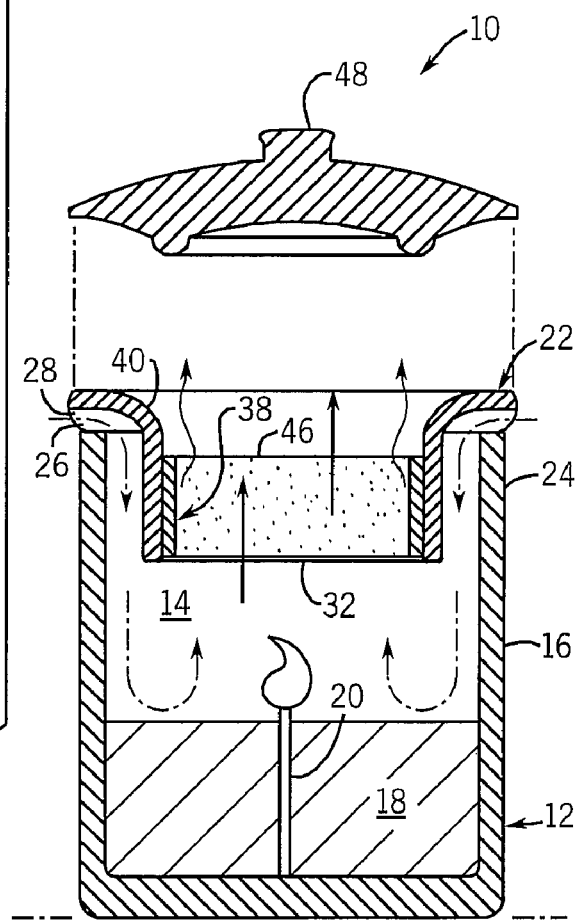
FIG. 4 is a view similar to FIG. 3 but of a second embodiment.

With reference to FIG. 4, there is shown a second embodiment of the present invention. (In FIG. 4 and the remaining figures showing embodiments alternative to that shown in FIGS. 1-3, parts of like function and structure may be given the same reference numbers as are used in FIGS. 1-3.) The second embodiment illustrates the use of a vertically extending sleeve 46 as the substrate that can be impregnated or coated with the air treatment chemical 38 to be dispensed. The sleeve 46 lines the opening 32 of the cover plate. The sleeve 46 may be affixed to the opening 32, creating a disposable lid 22, or it may be replaceable, serving as a refill for a permanent lid. The opening 32, in the second embodiment, extends deeper into the internal cavity 14 but, in the embodiment of FIG. 4, also is wide with respect to the overall size of the housing 12. The one feature can bring the sleeve 46 closer to a potentially hotter location, while the other can be a design feature that holds the sleeve further away from the burning wick 20. This illustrates some of the design features that can be selected to influence the temperature to which the sleeve 46 is exposed.

Alternatively, snuffer top 48 can be provided for extinguishing the combustion of the wax 18 when desired. Thus, the device could be used for a time, then snuffed, and then re-lit for a subsequent use period.

Figure 5:
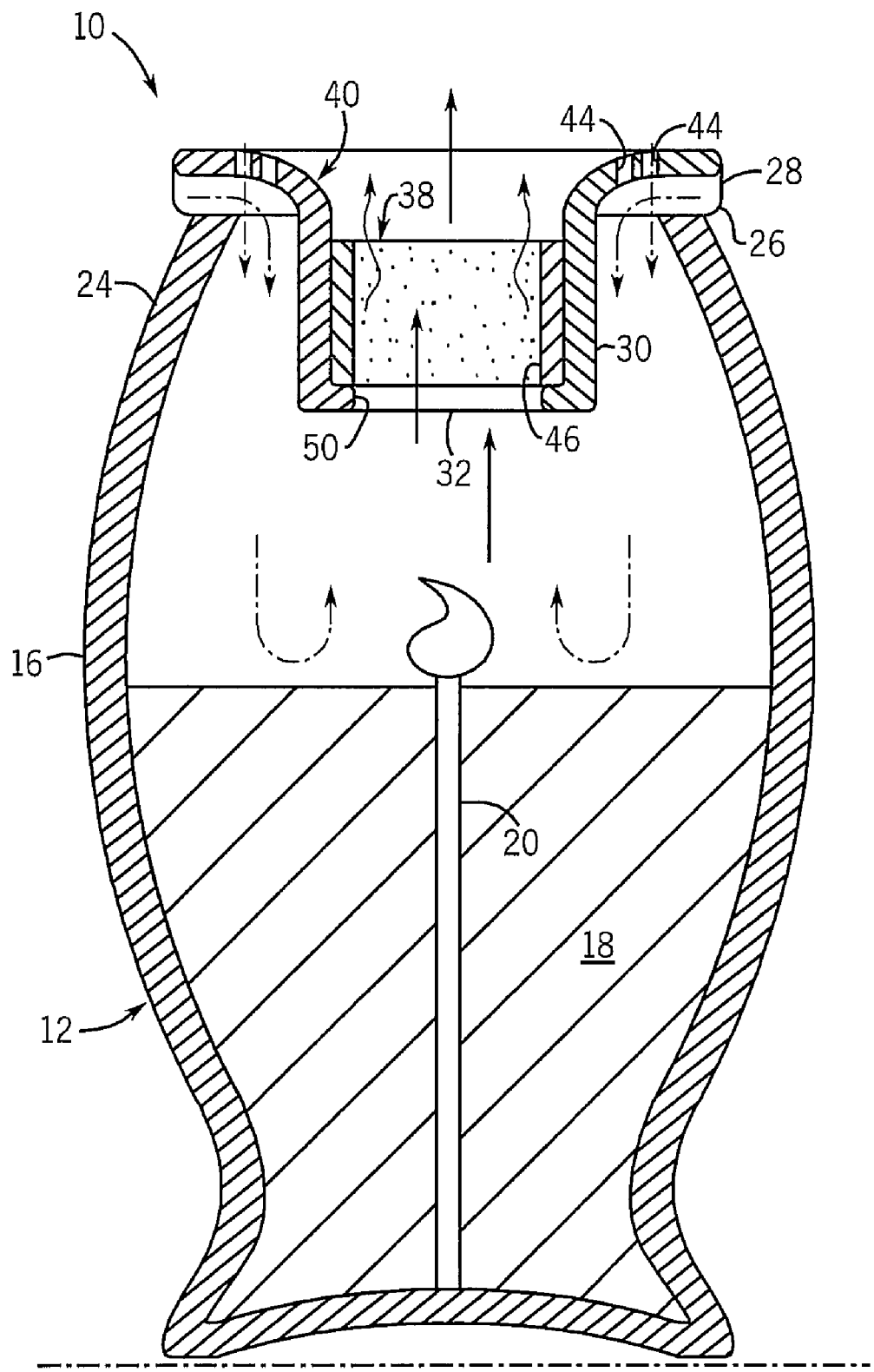
FIG. 5 is a view similar to FIG. 4, but of a third embodiment.

FIG. 5 has much in common with the FIG. 4 embodiment, albeit it is taller and thus can accommodate more wax 18. Note also an impregnated sleeve 46 sits on an annular ledge 50, both protecting its lower edge from direct exposure to the heat of the burning wick 20 and facilitating the use of a succession of replaceable sleeves that can be slid into place as the air treatment chemical 38 of a previous sleeve becomes exhausted. Cooler air is again funneled in through the air gap 28 and apertures 44 into the internal cavity 14 where it is heated and expelled through the chimney opening 32. As the warm air passes through the opening 32, the air treatment chemical 38 is heated and dispensed via the convection current created by the burning candle 10.

Figure 6:
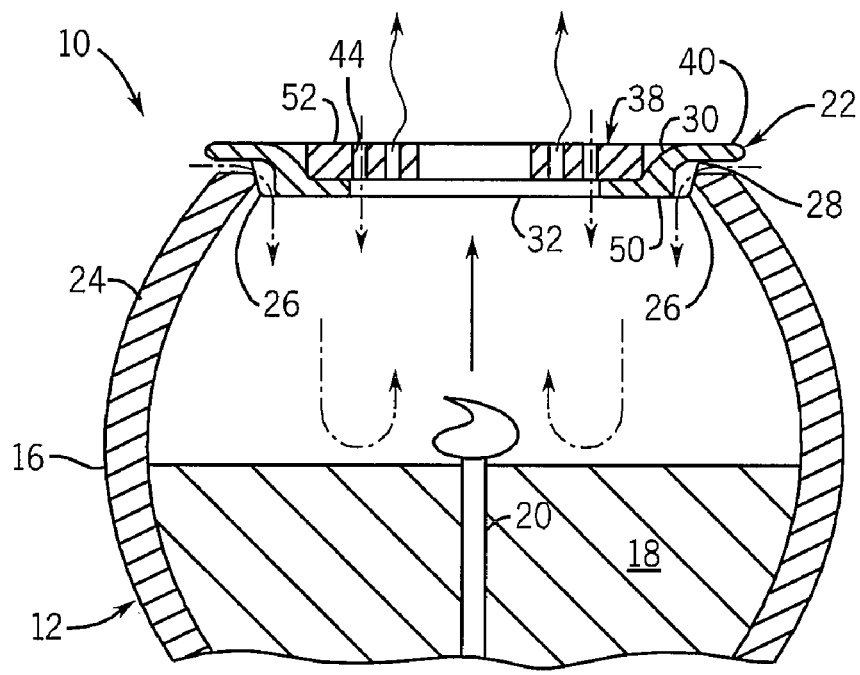
FIG. 6 is a view similar to FIG. 5, but of a fourth embodiment.

FIG. 6 shows a related design but with the air treatment chemical 38 coated onto a differently shaped, more disk-like ring 52. The ring 52 is suspended by annular ledge 50, similar to the arrangement shown in the embodiment of FIG. 5.

Figure 7:
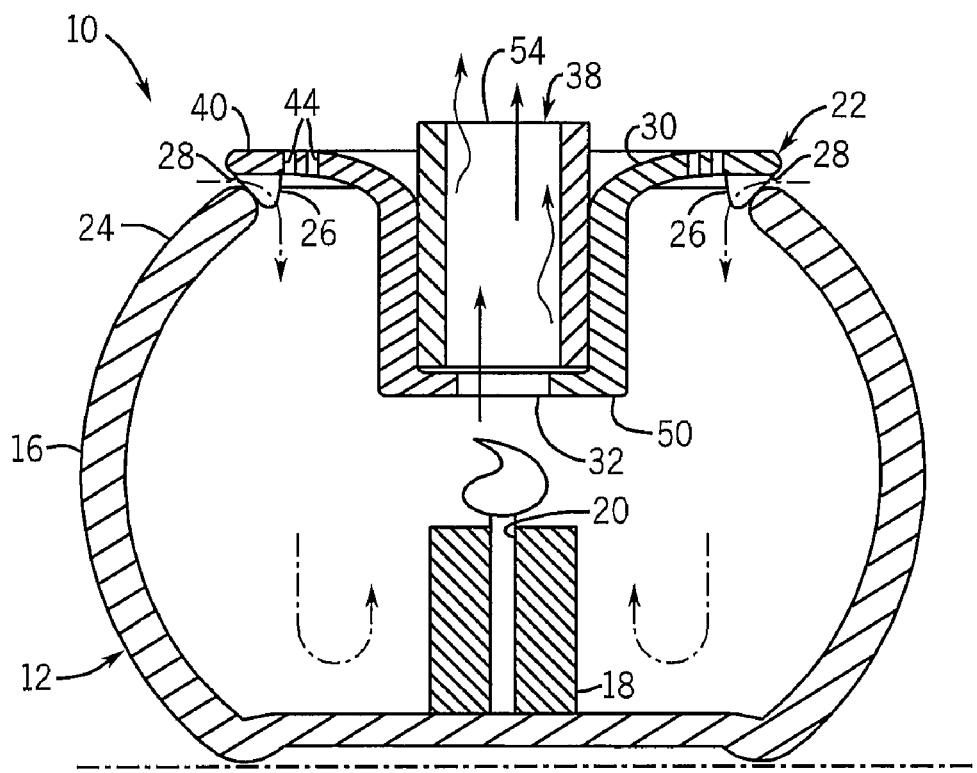
FIG. 7 is a view similar to FIG. 6, but of a fifth embodiment.

Turning to FIG. 7, this embodiment has an opening 32 and an annular ledge 50 supporting a differently shaped sleeve 54. The sleeve 54 is coated or impregnated with an air treatment chemical 38. The sleeve 54 extends above the upper surface 40 of the lid 22 to allow a consumer to easily remove and replace the sleeve 54 as needed or desired.

Figure 8:
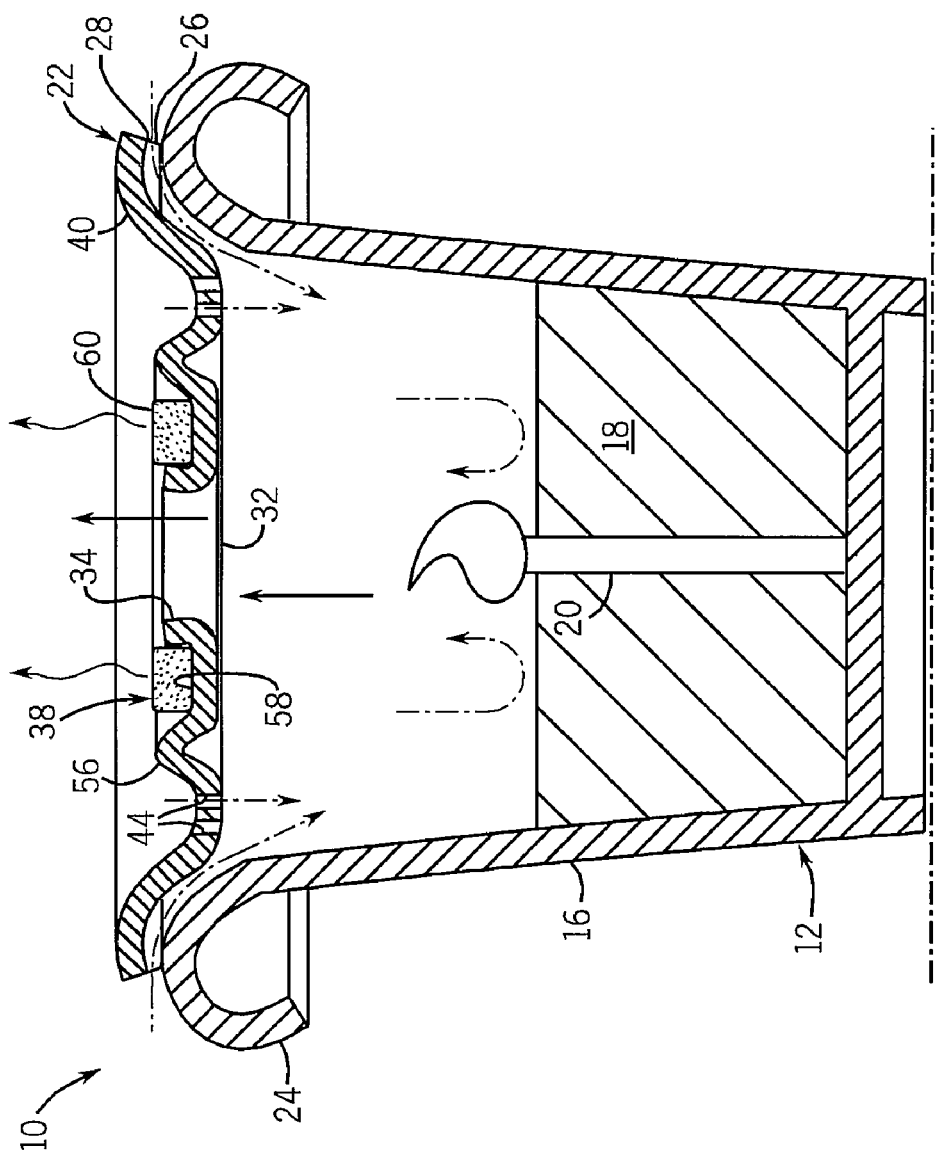
FIG. 8 is a view similar to FIG. 7, but of a sixth embodiment.

The FIG. 8 embodiment has a housing 12 in a form somewhat analogous to that used in commercially available citronella bucket-style candles sold for use in patios and other outdoor locations. The lid 22 has an undulation 56 forming a depressed pocket 58 in the plate 30 adjacent the opening 32. A ring 60 is held in the pocket 58 and is impregnated with an insect repellant such as d-cis/trans allethrin. Citronella is known to have only modest mosquito repelling efficacy. By means of the arrangement shown, the overall efficacy of the product can be increased, at the user's option, in response to a heavy mosquito pressure.

Figure 10:
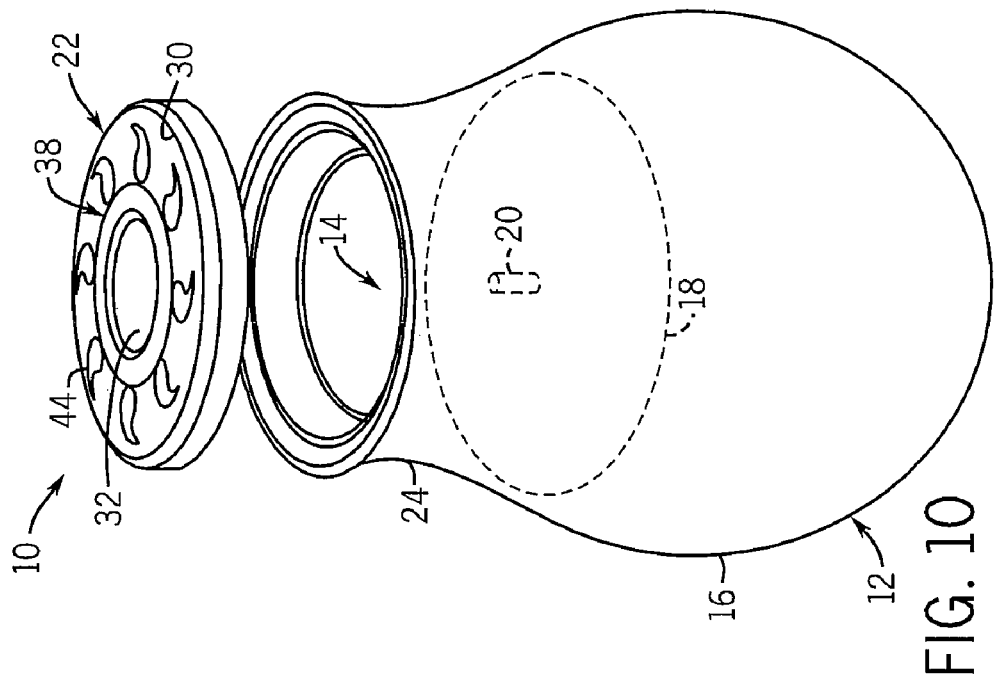
FIG. 10 is a view similar to FIG. 9, but of an eighth embodiment.
Figure 9:
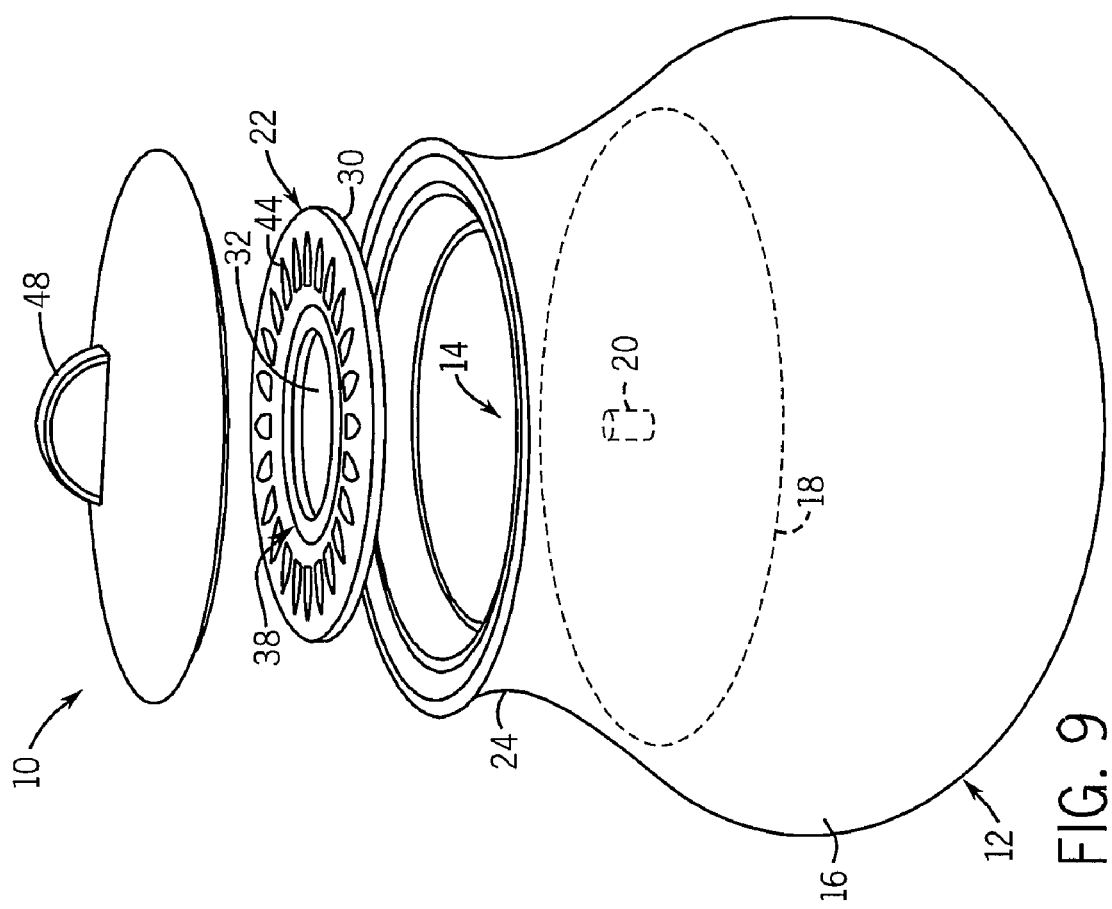
FIG. 9 is a view similar to FIG. 2, but of a seventh embodiment.

While the above describes preferred embodiments, it should be appreciated that other embodiments are also within the scope of the invention. For example, turning to FIGS. 9 and 10, two additional example embodiments are illustrated. Each includes a lid 22 having a cover plate 30 with a centrally disposed opening 32. Proximate the opening 32, the plate 30 bears an air treatment chemical 38. Apertures 44 provide the air gap 28, allowing cooler air to enter the internal cavity 14 before being heated and expelled past the air treatment chemical 38 as the heated air passes into the surrounding environment.

Thus, the claims that follow should be looked to in order to judge the full scope of the invention.

INDUSTRIAL APPLICABILITY

The present invention provides candles for dispensing air treatment chemicals where at least one such air treatment chemical is not mixed in with the wax.

What is claimed is:

1. An article for dispensing an air treatment chemical, the article comprising:
   a housing having a side wall structure, an upper lid, and an internal cavity in which is positioned a wax candle having a wick;
   the lid comprising:
      a cover plate to bear the air treatment chemical;
      an opening centrally disposed in the plate suitable to allow heated air to pass there through when the candle is being combusted, the opening being positioned over the wick;
      the plate being suspended across an upper end of the side wall structure such that there is an air passage adjacent the periphery of the plate other than through the plate;
   wherein the plate supports a substrate around the centrally disposed opening that is impregnated or coated with a supply of the air treatment chemical, the plate supporting the substrate so that it extends over a top of the candle; and
   wherein in addition to the centrally disposed opening the plate includes an inlet aperture through it;
   whereby, when the candle is combusted, the air treatment chemical can be heated thereby and carried away by heated air that has passed through the opening that is centrally disposed, and both the air passage and the inlet aperture can permit cooler air to enter the internal cavity while the candle is being combusted; and
   wherein a cap is removably positionable over the lid for covering the central opening and inlet aperture while keeping the air passage open.

2. The article of claim 1, wherein there is an undulation along an upper surface of the plate and the air treatment chemical is mounted in the undulation.

3. The article of claim 1, wherein the air treatment chemical is held by a ring form of the substrate that surrounds the centrally disposed opening.

4. The article of claim 1, wherein the air treatment chemical is held by a sleeve form of the substrate that lines the opening.

5. The article of claim 1, wherein the candle has mixed therein a second air treatment chemical that is different from the air treatment chemical.

6. The article of claim 5, wherein the second air treatment chemical is a fragrance and the air treatment chemical is an insect control agent.

7. The article of claim 1, wherein the air treatment chemical is selected from the group consisting of volatile insect control agents, fragrances, disinfectants, sanitizers, and deodorizers.

8. An article for dispensing an air treatment chemical, the article comprising:
   a housing having a side wall structure, an upper lid, and an internal cavity in which is positioned a wax candle having a wick;
   the lid comprising:
      a cover plate to bear the air treatment chemical;
      an opening centrally disposed in the plate suitable to allow heated air to pass there through when the candle is being combusted, the opening being positioned over the wick;
      the plate being suspended across an upper end of the side wall structure such that there is an air passage adjacent the periphery of the plate other than through the plate;
   wherein the plate supports a substrate around the centrally disposed opening that is impregnated or coated with a supply of the air treatment chemical, the plate supporting the substrate so that it extends over a top of the candle; and
   wherein in addition to the centrally disposed opening the plate includes an inlet aperture through it;
   whereby, when the candle is combusted, the air treatment chemical can be heated thereby and carried away by heated air that has passed through the opening that is centrally disposed, and both the air passage and the inlet apertures can permit cooler air to enter the internal cavity while the candle is being combusted;
   wherein: the article is configured such that, when the wax is combusted:
   the air treatment chemical can become essentially depleted from the substrate just as there becomes insufficient wax to support further burning of the candle; and
   wherein a cap is removably positionable over the lid for covering the central opening and inlet aperture while keeping the air passage open.

* * * * *